(12) United States Patent
Timpone et al.

(10) Patent No.: US 11,788,932 B2
(45) Date of Patent: Oct. 17, 2023

(54) SNAP BUTTON DEVICE FOR NON-DESTRUCTIVE CHARACTERIZATION OF MATERIALS

(71) Applicants: Francesco Timpone, Naples (IT); Aleksandr Sakhnevych, Naples (IT); Flavio Farroni, Modena (IT)

(72) Inventors: Francesco Timpone, Naples (IT); Aleksandr Sakhnevych, Naples (IT); Flavio Farroni, Modena (IT)

( * ) Notice: Subject to any disclaimer, the term of this patent is extended or adjusted under 35 U.S.C. 154(b) by 530 days.

(21) Appl. No.: 16/975,567

(22) PCT Filed: Feb. 4, 2019

(86) PCT No.: PCT/IB2019/050858
§ 371 (c)(1),
(2) Date: Aug. 25, 2020

(87) PCT Pub. No.: WO2019/171183
PCT Pub. Date: Sep. 12, 2019

(65) Prior Publication Data
US 2020/0400532 A1    Dec. 24, 2020

(30) Foreign Application Priority Data

Mar. 7, 2018   (IT) .................. 202018000002034

(51) Int. Cl.
*G01M 17/02*     (2006.01)
*G01N 3/307*     (2006.01)
*G01N 3/48*      (2006.01)
*G01N 33/44*     (2006.01)

(52) U.S. Cl.
CPC ............ *G01M 17/02* (2013.01); *G01N 3/307* (2013.01); *G01N 3/48* (2013.01); *G01N 33/445* (2013.01); *G01N 2203/0035* (2013.01); *G01N 2203/0094* (2013.01)

(58) Field of Classification Search
None
See application file for complete search history.

(56) References Cited

U.S. PATENT DOCUMENTS 5,485,084 A *  1/1996  Duncan .............. G01N 27/9053
                                                      324/225
7,034,660 B2 * 4/2006  Watters .............. G01M 5/0008
                                                      205/777

(Continued)

*Primary Examiner* — Peter J Macchiarolo
*Assistant Examiner* — Jermaine L Jenkins
(74) *Attorney, Agent, or Firm* — R. Ruschena Patent Agent, LLC

(57) ABSTRACT

A device for nondestructive viscoelastic characterization of materials, comprising: a tubular shell, having inside a through-recess provided with at least a first and a second shrinkage; a first rod, provided with a base of ferromagnetic material (8), sliding inside said shell between a first position, in which said ferrule does not project to the lower base of said shell, and a second position, in which said ferrule projects to said lower base; a first spring configured to push said ferrule outwards; a displacement sensor configured to read the displacement of said first rod; a button, sliding-between a stroke greater than the one of said first rod, and integral to a second rod provided with a magnet and coaxial to said first rod; a second spring.

5 Claims, 3 Drawing Sheets

(56) References Cited

U.S. PATENT DOCUMENTS

| | | | |
|---|---|---|---|
| 8,789,410 B2 * | 7/2014 | Dardelin | G01N 27/9013 73/146 |
| 10,408,796 B2 * | 9/2019 | Bondurant | B06B 1/045 |
| 2016/0266068 A1 * | 9/2016 | Boenisch | G01N 27/904 |

* cited by examiner

SNAP BUTTON DEVICE FOR NON-DESTRUCTIVE CHARACTERIZATION OF MATERIALS

BACKGROUND OF THE INVENTION

1. Field of the Invention

The present invention relates to the technical field comprising measurement devices used for viscoelastic characterization of materials, and in particular of tires for vehicles.

The present invention aims at developing a measurement device which provides parameter values called storage modulus, loss modulus and loss factor of a tire which define their viscoelastic features.

2. Brief Description of the Prior Art

The storage modulus measures the stored energy and is linked to the elastic behavior. The loss modulus measures the dissipated energy and is linked to the viscoelastic behavior.

The ratio between loss modulus and storage modulus provides the phase angle tangent between the two modules.

Such aim is reached by means of a device comprising the features described in the main claim. Advantageous embodiments of the invention are described in the dependent claims.

At the state of the art there are known and commonly used measurement devices which provide an index allowing to provide information about similarity between various types of tires. An example is described in the Patent FR2846094A1, where the tire features are defined by using a load and a spring to provide impact at a test temperature T. After impact the tire is deformed and so it is obtained the elastic modulus of the material the tire is made up of. As a consequence, the energy loss is known, and by using a computer it is possible to provide the characteristic curve of the material of the tire. The soil roughness curve is obtained by a spectrometer and matched to the curve of the tire.

Disadvantageously however the load is released manually by the operator. In this way, it is not sure that the potential energy is always the same, in fact the operator could slow the load falling by using fingers. As a consequence, the calculation of the material index is not exact since the impact speed is not always the same but subjected to a possible mistake of the operator, therefore it can be said that such a system is operator-dependent. There exist also other measurement systems whose architecture is more complex and requires test benches which make these systems cumbersome and very expensive.

Therefore, there remains unresolved the problem to provide a device for viscoelastic characterization of materials, and in particular of tires, which overcomes the limits of the devices known at the state of the art, and which is in particular cheap, portable and which allows to obtain test results nondependent on the operator manual skill.

SUMMARY OF THE INVENTION

According to a first aim the present invention provides a portable device which allows the viscoelastic characterization of a material by providing storage modulus, loss modulus and loss factor values.

According to another aim the present invention provides a device for viscoelastic characterization of materials which allows to apply a constant potential energy to the material during the various repetitions of a measurement, without such value being influenced by the operator who is using the device.

According to another aim the present invention provides a device for viscoelastic characterization of materials which allows to vary the potential energy applied to the test material simply by replacing a spring with another one with different rigidity.

Yet, according to another aim the present invention provides a device for viscoelastic characterization of materials which allows to vary the free motion frequency but not the forced motion frequency in order to provide a device with the fewest elements possible, and so cheap, functional and portable.

Yet, according to another aim the present invention provides a device for viscoelastic characterization of materials which allows to vary the temperature of the material under characterization, in order to increase the discrete points defining the viscoelastic characteristic curve of the material.

Yet, according to another aim the present invention provides a portable device for viscoelastic characterization of materials which allows to control that the device is perfectly orthogonally positioned to the tire or which allows, while processing data detected, to consider the angle between the trajectory of the mass stroke striking against the tire and the direction of the load force in order to have a defined fall force.

The present invention reaches the prefixed aims since it is a device for nondestructive viscoelastic characterization of materials, comprising: a tubular shell (1), almost cylindrically shaped and such dimensioned that it can be grasped by hand, having inside a through-recess provided with at least a first shrinkage (19) provided inside the axial development of said inner recess and a second shrinkage (5) provided at the upper base of said shell (1); a first rod (2), provided at an end with a cap (18) and a ferrule (11) projecting to the same, and at the other end with a base of ferromagnetic material (8), fastened so that it can slide inside said shell (1) between a first position, in which said ferrule (11) does not project to the lower base (12) of said shell (I), and a second position, in which said ferrule (II) projects to the said lower base (12);—a first spring (20) configured to push said ferrule (11) of said rod (2) outwards, from the side of said lower base (12);—a displacement sensor (10) configured to read the displacement of said first rod (2) while sliding along the tubular shell (1); a button (3), sliding between a first and a second position inside said shell (1) with a stroke greater than the one of said first rod (2), and integral to a second rod (21) coaxial to said first rod (2) said second rod (21) being provided, at the end facing said first rod (2), with a magnet (7); a second push spring (6), with elastic rigidity greater than said first spring (20) configured to push said button (3) to the upper portion of said tubular shell (1), said device being configured so that after pressing the button (3) said magnet (7) comes in contact to said base of ferromagnetic material (8), thus fastening it by magnetic attraction, and so that after the button is released said base of ferromagnetic material is separated from sard magnet (7) when said stop (9) prevents another movement of said first rod (2), thus allowing said first rod (2) to fall freely always at the same height.

BRIEF DESCRIPTION OF THE DRAWINGS

The invention will be described in the following with reference to the appended FIGS. 1 to 3.

DETAILED DESCRIPTION OF THE INVENTION

Figure 1:
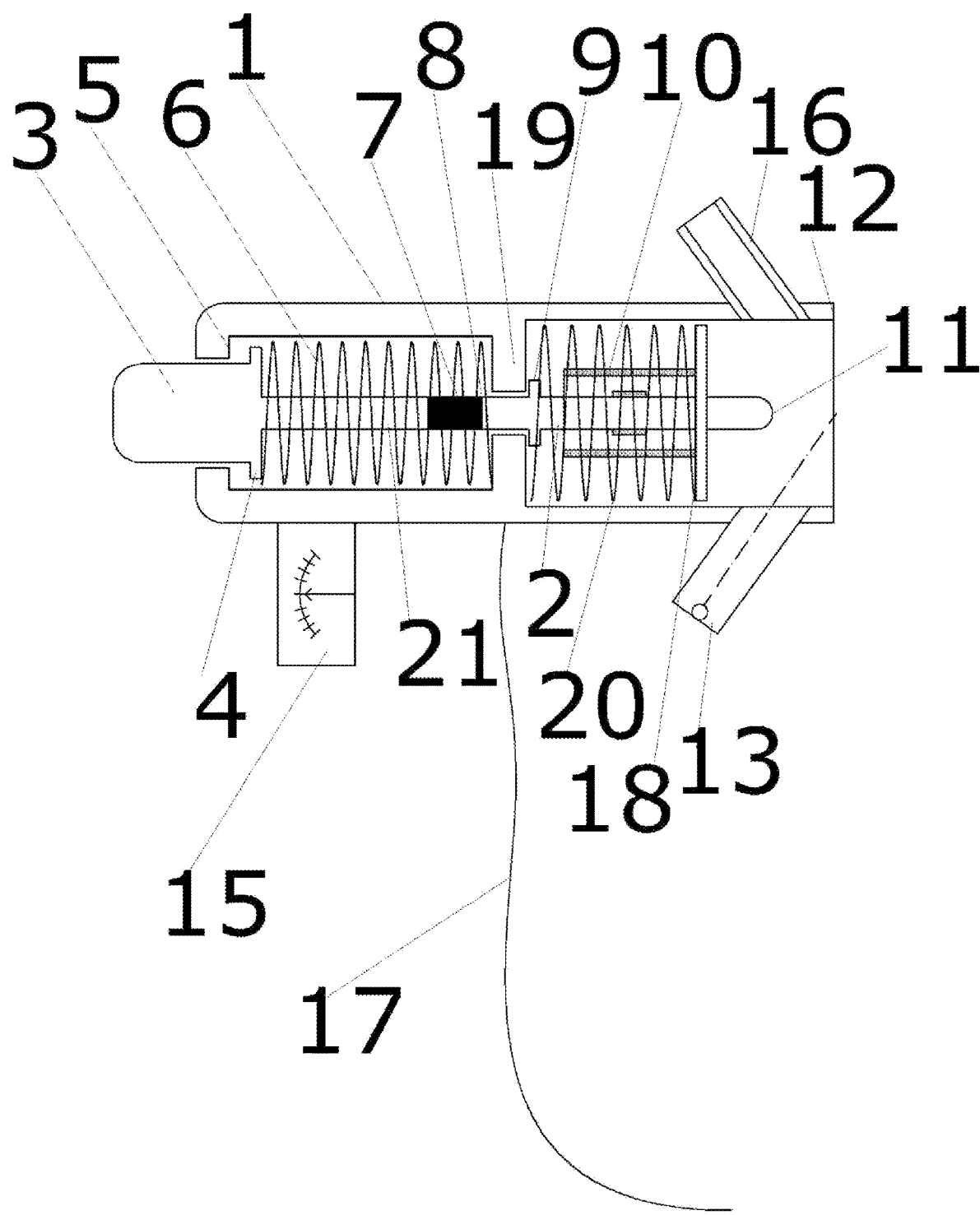
In FIG. 1 it is shown a section view of a preferred embodiment of the invention with all its essential elements, wherein the button (3) is positioned where the magnet (7) is detached from the base of ferromagnetic material (8)
Figure 2:
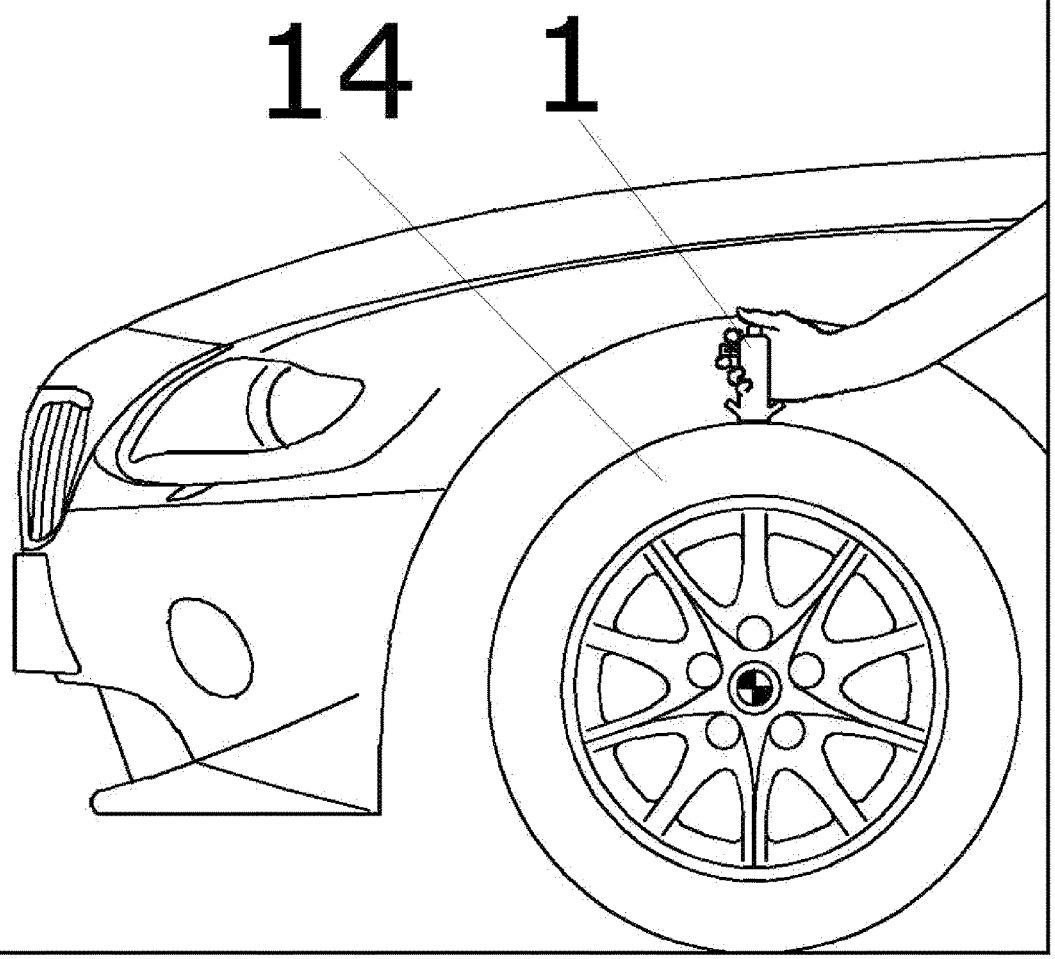
in FIG. 2 it is shown a view of a usage of the invention showing the measurement by putting the tubular shell (1) on a tire (14)
Figure 3:
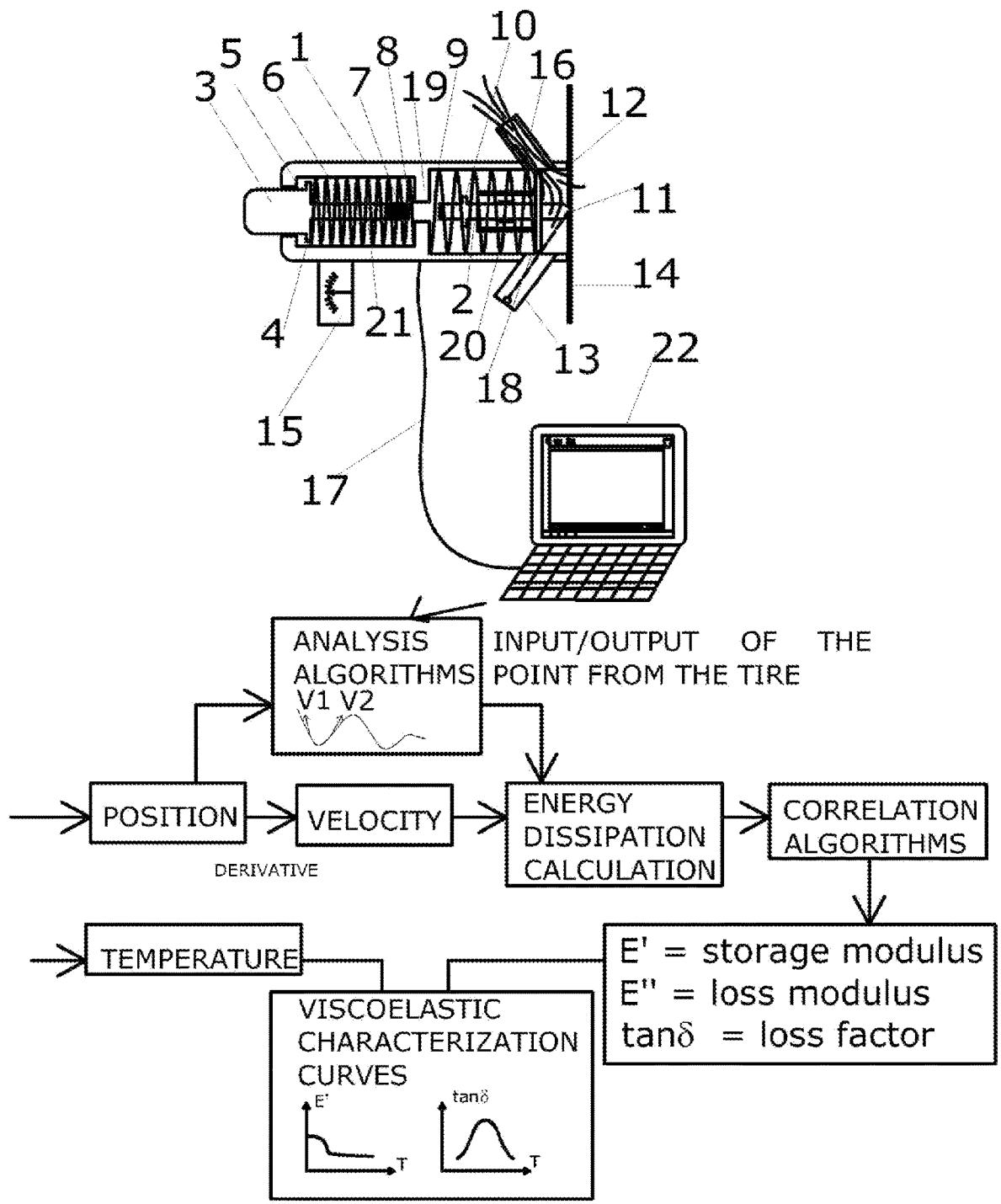
in FIG. 3 it is shown a view of another usage of the invention showing how the viscoelastic features of a tire (14) are obtained by means of position and temperature data processed by a computer (22). In the figure it is represented the magnet (7) detached from the base of ferromagnetic material (8) and a scheme of how the data are processed by the computer (22).

As it is shown in the appended FIG. 1, the device for nondestructive viscoelastic characterization of materials according to the invention comprises:
- a tubular shell (1), almost cylindrically shaped and such dimensioned that it can be grasped by hand, having inside a through-recess provided with at least a first shrinkage (19), also called step, provided inside the axial development of said inner recess and a second shrinkage (5) provided at the upper base of said shell (1);
- a first rod (2), provided at an end with a cap (18) and a ferrule (11) projecting to the same, and at the other end with a base of ferromagnetic material (8). The rod (2) is fastened so that it can slide inside said shell (1) between a first position, in which said ferrule (11) does not project to the lower base (12) of said shell (1), and a second position, in which said ferrule (11) projects to the said lower base (12). To such end the rod (2) is provided with a stop; (9) configured to abut said shrinkage (19), this limiting said rod stroke towards the upper portion of said shell;
- a first spring (20) compressed between said cap (18} and said shrinkage {19) and configured to push said ferrule (11) of said rod (2) outwards, from the side of said lower base (12); said first spring (20) being integral to said cap (18) so that the stroke of said ferrule towards the lower portion of said shell is limited;
- a displacement sensor (10) configured to read the displacement of said first rod (2) while sliding along the tubular shell (1). Conveniently said sensor (10) is positioned inside said tubular shell (1);
- a button (3), which can be actuated from outside from the upper end of said shell (1) and sliding inside said shell (1) with a greater stroke than the one the first rod (2). Th button (3) is integral to a second rod (21) coaxial to said first rod (2) and provided, at its end facing said first rod (2), with a magnet (7). Conveniently said button (3) is integral to a second cap (4) configured to abut said second shrinkage (5) to limit the stroke of said button, thus preventing the same from completely going out from said shell??????

(1); —a second push spring (6), with elastic rigidity greater than the first spring (20), arranged inside said tubular shell (1) and compressed between said shrinkage (19) and said second cap (4), so to push said button (3) towards the upper portion of said tubular shell (1), thus maintaining the upper portion outside.

After describing the various elements, it is now possible to describe the device functioning.

According to what described the device is configured so that when the button (3) is pressed, the magnet (7) comes in contact to the base of ferromagnetic material (8), which remains fastened to the magnet (7) by magnetic attraction. The force of the magnet (7) and the rigidity of the first spring (20} are configured so that said magnet (7) has a magnetic force greater than the compression force exerted by the spring (20). Therefore, while the button (3) is released, said second spring (21) pushes the whole system towards the upper portion, until said stop (9) prevents another movement of said first rod (2). Since the stroke allowed to the button (3) is greater than the stroke allowed to the first rod (2), this will continue in its stroke upwards pushed by the second spring (21), thus causing the mechanical detachment of the magnet (7) from the base of ferromagnetic material (8) always at the same point.

Therefore, the first rod (2) can fall freely, always at the same height. Such event guarantees that, in all the measurements, the potential energy of the first rod (2) is always the same, since the detachment is mechanical and does not depend on the operator.

Conveniently, the device comprises also a computer (22) connected to said displacement sensor (10) by means of a suitable connector (17). The computer (22) processes data after acquiring the development in time of the position of ferrule (11), as input signals. By means of an analysis algorithm, known at the state of the art, it calculates the energy dissipated and provides the storage modulus, loss modulus and loss factor parameter values of a tire, which define its viscoelastic features.

Preferably but not limitingly, the device further comprises a temperature sensor (13), integral to the tubular shell (1), configured so that the temperature of the tire area is detected and communicated to said computer in the test step, i.e. the area of the tire where the impact of the ferrule (11) occurs. Preferably said temperature sensor is of infrared type and is configured to detect said temperature without coming in contact to said tire;

Moreover, according to another embodiment the device comprises, integral to the tubular shell (1), a channel (16) arranged at the contact area between ferrule (11) and (tire (14) for inputting hot air or cold air, which allows to vary the test temperature in order to increase the concrete points which define the viscoelastic characteristic curve of the material.

Moreover, preferably, in order to guarantee that the fall force of the first rod (2) is always constant, the device can comprise, integral to said tubular shell (1), an inclinometer (15) configured to read the angle between the vertical (direction of the load force) and the axis of the first rod (2), so that the test can be carried out by always maintaining the same angle o by considering it in the calculation.

By varying the frequency of the mass-spring system as well as the test temperature there can be obtained more points defining the viscoelastic curve of the material the tire is made up of. In order to vary the frequency of the mass/spring system said first spring (20) can be conveniently replaced.

The invention claimed is:
1. A device for nondestructive viscoelastic characterization of materials, comprising:
   a tubular shell (1), cylindrically shaped and such dimensioned that the tubular shell is capable of being grasped by hand, having inside a through recess provided with at least a first shrinkage (19) provided inside the axial development of said through recess and a second shrinkage (5) provided at an upper base of said tubular shell (1);
   a first rod (2) provided at an end with a cap (18) and a ferrule (11) projecting to the same, and at the other end with a base of ferromagnetic material (8), fastened so that the first rod (2) can slide inside said tubular shell (1) between a first position, in which said ferrule (11) does not project to the lower base (12) of said tubular shell (1), and a second position, in which said ferrule (11) projects to the said lower base (12); a first spring (20) configured to push said ferrule (11) of said first rod (2) outwards, from the side of said lower base (12);

a displacement sensor (10) configured to read the displacement of said first rod (2) while sliding along the tubular shell (1); a button (3) sliding between a first and a second position inside said tubular shell (1) with a stroke greater than the one of said first rod (2), and integral to a second rod {21} coaxial to said first rod (2), said second rod (21) being provided, at the end facing said first rod (2), with a magnet (7);

a push spring (6), with elastic rigidity greater than said first spring (20) configured to push said button (3) to an upper portion of said tubular shell (1), said device being configured so that after pressing the button (3) said magnet (7) comes in contact to said base of ferromagnetic material (8), thus fastening the magnet (7) by magnetic attraction, and so that after the button is released, said base of ferromagnetic material is separated from said magnet (7) when a stop (9) prevents another movement of said first rod (2), thus allowing said first rod (2) to fall freely always at the same height.

2. The device for nondestructive viscoelastic characterization of materials according to claim 1, further comprising a computer (22) connected to said displacement sensor (10) by means of a suitable connector (17), and configured to process data detected by said sensor by calculating at least a parameter relating the viscoelastic characterization of the material.

3. The device for nondestructive viscoelastic characterization of materials according to claim 1, further comprising a temperature sensor (13), integral to the tubular shell (1), and configured so that thea temperature of a tire area is detected which is an area where an impact of said ferrule (11) occurs and communicated to said computer in a test step.

4. The device for nondestructive viscoelastic characterization of materials according to claim 1, further comprising, integral to the tubular shell (1), a channel (16) arranged at a contact area between the ferrule (11) and a tire (14) for inputting hot air or cold air, which allows to vary a test temperature in order to increase concrete points which define a viscoelastic characteristic curve of the material.

5. The device for nondestructive viscoelastic characterization of materials according to claim 1, further comprising, integral to said tubular shell (1), an inclinometer (15) configured to read an angle between a vertical and a sliding axis of said first rod (2).

* * * * *